United States Patent [19]

Chazan et al.

[11] 4,031,210
[45] June 21, 1977

[54] ANTIBIOTIC AMINOGLYCOSIDES, PROCESSES OF PREPARATION AND PHARMACEUTICAL COMPOSITIONS

[75] Inventors: Jean-Bernard Chazan, Paris; Jean-Claude Gasc, Bondy, both of France

[73] Assignee: Roussel-UCLAF, Paris, France

[22] Filed: Nov. 11, 1975

[21] Appl. No.: 630,917

[30] Foreign Application Priority Data

Nov. 13, 1974 France .............................. 74.37374

[52] U.S. Cl. ................................ 424/180; 536/17; 536/4
[51] Int. Cl.² ................. C07H 15/22; A61K 31/71
[58] Field of Search ............. 260/210 AB; 424/180; 536/17

[56] References Cited

UNITED STATES PATENTS 3,925,354  12/1975  Umezawa et al. ........... 260/210 AB
3,929,762  12/1975  Umezawa et al. ........... 260/210 AB

*Primary Examiner*—Johnnie R. Brown
*Attorney, Agent, or Firm*—Bacon & Thomas

[57] ABSTRACT

There are disclosed pharmaceutically-active aminoglycosides comprising 4-O-[2',6'-diamino 2',3',6'-tridesoxy α,D-ribohexopyranosyl] 6-O-[3''-methylamino 3'',4'',6''-tridesoxy α,D-xylohexopyranosyl] 2-desoxystreptamine of the formula:

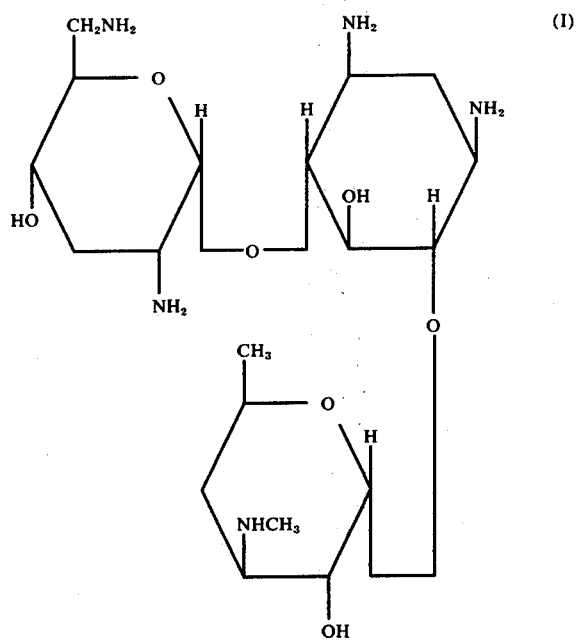

and the addition salts thereof with mineral acids or organic acids. Also disclosed are methods for preparation of the novel products as well as certain novel intermediate products. There are also disclosed pharmaceutical compositions in which the novel products are the active agents and a method for the treatment of bacteria infections in humans and animals.

9 Claims, No Drawings

ANTIBIOTIC AMINOGLYCOSIDES, PROCESSES OF PREPARATION AND PHARMACEUTICAL COMPOSITIONS

The present invention concerns new derivatives of Aminoglycosides and their process of preparation. These compounds are pharmaceutically active as antibiotics. Thus, the main object of the present invention is new derivatives of Aminoglycosides, namely,

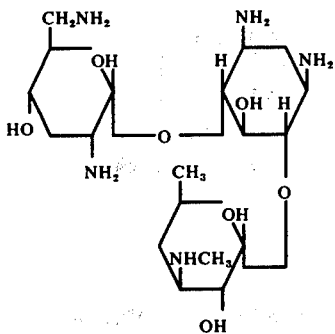

as well as addition salts thereof with mineral or organic acids. These salts may be obtained by the complete or partial neutralization of the five amino functional groups.

Such addition salts include, for example, hydrochloride, hydrobromide, nitrate, sulfate, phosphate, acetate, formate, benzoate, maleate, fumarate, succinate, tartrate, citrate, oxalate, benzylate, glyoxylate, aspartate, alkanesulfonate such as methane sulfonate, arylsulfonate such as p-toluene sulfonate, or the like which are formed by using the corresponding acid.

Another object of the invention is the provision of pharmaceutical compositions particularly antibiotic compositions which include, as the active principle, the product of formula I or one of its therapeutically compatible salts.

The aforementioned products possess very interesting antibiotic activities on the bacteria gram (+) such as Staphylococci Streptococci and notably penicillin resistant Staphylococci as well as on the bacteria gram (−), and notably coliform bacteria. Thus, they are useful in the treatment of humans and animals which are affected by these bacteria.

These properties render the product of formula I as well as its therapeutically compatible salts suitable for use as medication notably in the treatment of staphylococci such as those which are responsible for blood poisoning, skin diseases and infections on the face, pyodermites, septic and running sores, anthrax or carbuncles, phlegmons, erysipelas and the like. Also, acute staphylococci which arises in both the early stages and after influenza, bronchopneumonia, and other infections of the lung including lung congestion can be treated by the products of this invention. Further, the products of the invention can be used against collibacilloses.

These products can be used parenterally, orally, rectally or locally by topical application on the skin or mucous membrane. They can be given, for example, in the form of injectable solutions or suspensions, sterile powders for improvised injectable preparations, tablets, capsules, syrups, suppositories, creams, pommades and aerosol preparations. These pharmaceutical forms are prepared according to the standard processes. The usual dose, varying according to the product used, the subject treated, and the affection concerned, can be from 100 mg to 1 gram per day in a normal human being when administered parenterally.

The novel method of the invention for treating bacteria infections in humans and animals comprises administering to humans and animals a therapeutically effective amount of the compound of formula I or one of its therapeutically compatible salts.

The invention also comprises a process of preparation of the product of formula I above and of its salts, the process including a novel sequence of steps.

This process is characterized in that the product of formula:

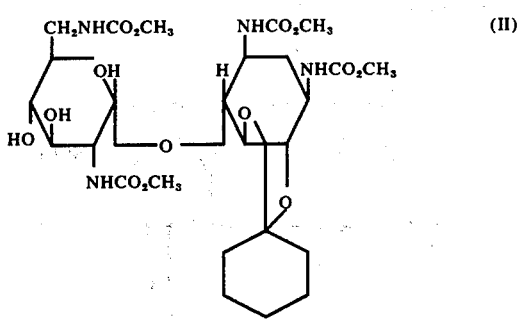

is reacted with tosyl chloride in the presence of an organic base to obtain a product of the formula:

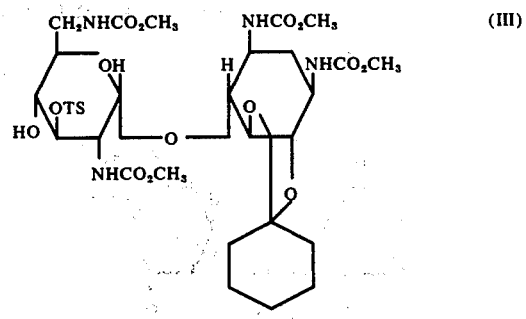

which is then treated with an alkaline iodide to obtain a product of the formula:

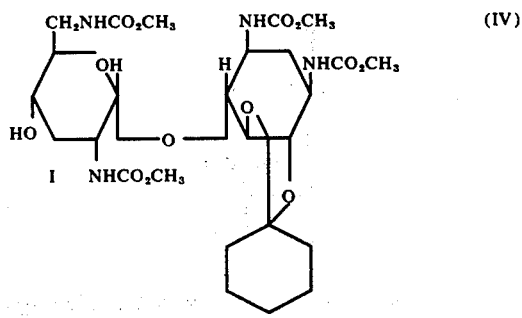

which is treated with hydrogen in the presence of a catalyst to obtain the product:

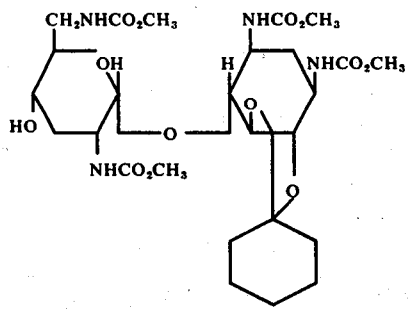
(V)

which was treated with acetic anhydride in the presence of an organic base to obtain the product having the formula:

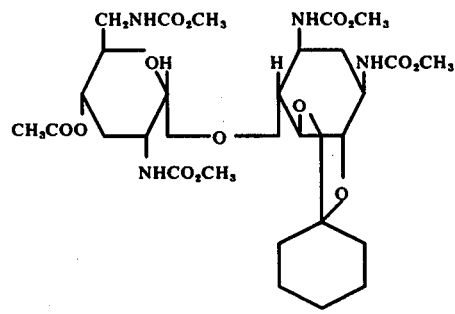
(VI)

which was reacted with an acidic agent to obtain a product of the formula:

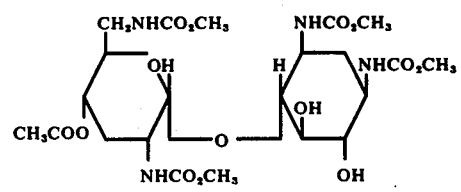
(VII)

which was reacted with a product having the formula:

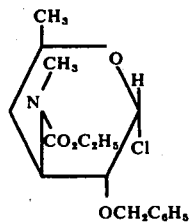
(VIII)

in the presence of a catalyst to obtain a condensation product as a mixture of α and β anomers having the formula:

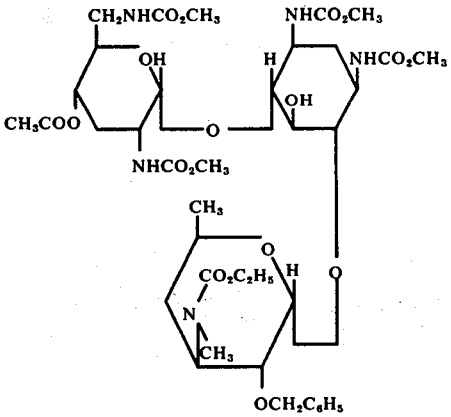
(IX)

and

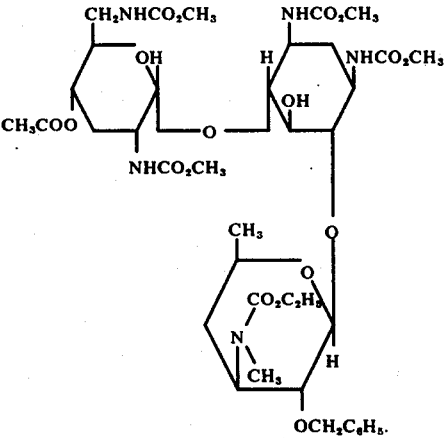
(IX')

The mixture was treated with hydrogen in the presence of a catalyst and the blocked amine and hydroxyl functions liberated by treatment of the mixture in an alkaline medium to obtain the mixture of products having the formulae:

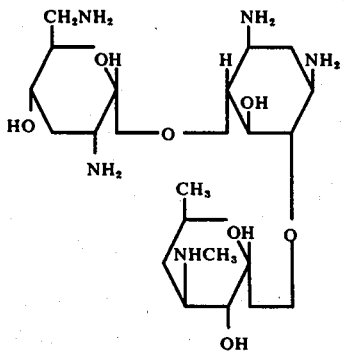
(I)

and

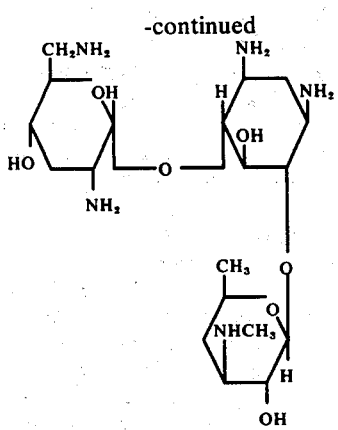

The product of formula I is separated from the mixture by conventional methods. If desired, the salts are formed by salification with an organic or inorganic acid.

In the above process, the hydrogenolysis and the hydrolysis leading to the products of formulae I and X from the products of formulae IX and IX', can be effected either beginning with the hydrogenolysis or with the hydrolysis.

The preferred operating conditions in the general process described above are as follows: The organic base in the presence of which the product of formula II is reacted with the tosyl chloride is preferably pyridine but other organic bases which may also be employed are for example lutidine or collidine and the like.

The alkaline iodide which is used to treat the product of formula III is preferably sodium or potassium iodide while the catalyst which is used when the product of formula IV is treated with hydrogen is preferably Raney nickel. However, other hydrogenation catalysts such as, for example, palladium, palladium salts or platinum derivatives may be used.

The organic base which is used during the reaction of acetic anhydride with the product of formula V is preferably pyridine, but other organic bases which may be used include lutidine, collidine or the like.

The acidic agent which is used to treat the product of formula VI is preferably aqueous acetic acid, but other organic acids which may be used include, for example, formic and oxalic acids. Also, aqueous solutions of inorganic acids such as hydrochloric and sulfuric acid may be used.

The reaction (condensation) between products VII and VIII is a named reaction referred to as KOENIGS-KNORR reaction, and is effected in the presence of a catalyst which is preferably mercuric cyanide. One can also use other mercury salts, a silver or cadmium salt, or a tertiary amine, such as collidine.

As the hydrogenation catalyst to transform the mixture of products of formula IX and IX' to a mixture of the reduced products, it is advantageous to use palladium deposited on carbon black, but one can also use other palladium salts or platinum, derivatives of platinum and other conventional catalysts such as rhodium, ruthenium or nickel.

The alkaline agent which may be used to liberate the amine functions and the esterified hydroxyl function is advantageously an aqueous alcoholic solution of baryta (barium hydroxide) but other aqueous bases such as aqueous sodium, potassium, or lithium hydroxide solutions may also be used.

The separation of the products of formulas I and X is obtained by conventional physical procedures. The separation may preferably be obtained chromatographically using silica but alumina, cellulose or magnesium silicate can be used. The separation can also be obtained by using fractional crystallization or countercurrent separation techniques. Different pure or aqueous organic solvents or mixtures of solvents may be used to satisfactorily make the separation.

The acid salt of compounds of formula I may be formed by conventional techniques. Acids which may be used for this include for example, hydrochloric, hydrobromic, nitric, sulfuric, phosphoric, acetic, formic, benzoic, maleic, fumaric, succinic, tartaric, citric, oxalic, benzylic, glyoxylic, aspartic, alkane sulfonic, and arylsulfonic acids. The salification is preferably obtained in a solvent or a mixture of solvents such as water, ethers, such as ethyl ether, alcohols, such as methanol or ketones such as acetone.

The product of formula VIII used in the process of the invention may be prepared according to the procedure as described in French Pat. No. 73 16 882 of May 10, 1973.

This process is characterized by reacting a compound having a formula:

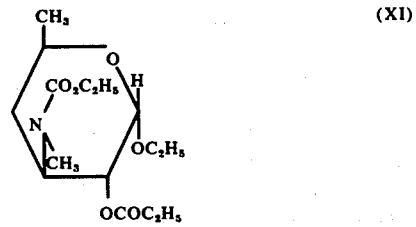

With an alkaline reagent at room temperature to obtain a product having the formula:

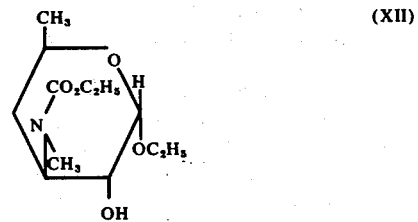

this product is then treated with a benzyl halide in the presence of an alkaline agent to obtain a compound of the formula:

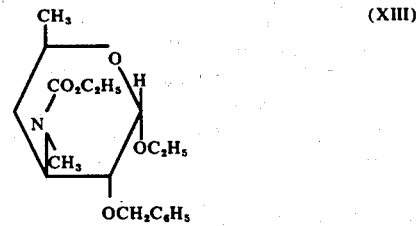

which is treated with acetic anhydride in acetic acid in the presence of a strong acid to obtain a product of the formula:

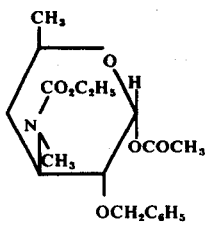

This product is then treated with anhydrous hydrochloric acid in the presence of acetyl chloride (an acyl halide) in an organic solvent medium to obtain the product of formula VIII.

The wavy line which connects the substituents on the carbon atom of the 1-position in formulae VIII, XI, XII, XIII and XIV indicates that these substituents may be either α or β to the ring. These products exist as the anomers α or β or as a mixture of these.

Another object of the invention is the intermediate compound having the following formula:

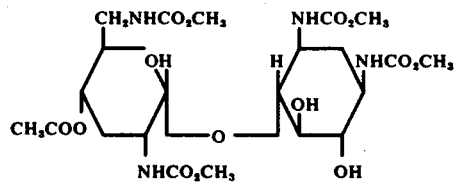

as well as the mixture of α and β anomers of formulae IX and IX' described above, which are particularly useful as intermediates in the preparation of compounds of formula I. The following examples illustrate the invention without in any way being limiting thereon.

EXAMPLE 1

4-0-[2',6'-diamino 2',3',6'-tridesoxy α, D-ribohexopyranosyl] 6-0-[3"-methylamino 3",4",6"-tridesoxy α, D-xylohexo-pyranosyl] 2-desoxy streptamine.

Stage A: 5,6-0-cyclohexylidene 3'-0-tosyl tetra-N-carbomethoxy neamine:

100 grams of 5,6-0-cyclohexylidene tetra-N-carbomethoxy neamine (prepared according to the procedure described in the Journal of Antibiotics, 1971, page 711) were dissolved in two liters of pyridine. The solution is cooled to 0° C and 150 grams of tosyl chloride is fractionally added over an hour. The reaction mixture is allowed to react ambient temperature and is stirred for 18 hours at 24° C. 52.5 grams of sodium formate were then added to the reaction mixture over 3 hours. The mixture is then concentrated under reduced pressure and the residue added to water. This aqueous mixture is extracted with chloroform, the organic phase is washed with water and dried over sodium sulfate. After evaporation of the solvent and drying under vacuum at 40° C, 112 grams of crystalline 5,6-0-cyclohexylidene 3'-0-tosyl tetra-N-carbomethoxy neamine which is used in the following steps was obtained. This product may be recrystallized by means of a mixture of ethyl acetate and ether.

Thin layer chromatography on silica with a 95:5 mixture of chloroform and methanol: Rf=0.3

Stage B: 5,6-0-cyclohexylidene 3'-desoxy 3'-iodo tetra-N-carbomethoxy neamine:

393 grams of sodium iodide is mixed with 790 ml of dimethylformamide. The mixture is heated to a temperature of 95° C and 76 grams of the product of the preceding stage is added to the solution obtained. The mixture is heated to 103° C for 16 hours, then, after cooling, 2.5 liters of methylene chloride was added. The precipitate washed with methylene chloride was dried. The filtrate was washed with water and the organic phase evaporated to dryness.

The residue crystalline material obtained from the methylene chloride was washed two times with an aqueous solution of methylene chloride and dried over magnesium sulfate. The methylene chloride is evaporated to dryness to obtain 50.2 grams of [5,6-0-cyclohexylidene 3'-desoxy 3'-iodo tetra-N-carbomethoxy neamine]which is used in the following Stage C.

Thin layer chromatography (silica, chloroform-methanol 95:5): Rf=0.4

Stage C: 5,6-0-cyclohexylidene 3'-desoxy tetra-N-carbomethoxy neamine:

47.7 grams of the product of the preceding stage (Stage B) 1.5 liters of methanol, 95 ml of triethylamine and about 300 ml of an aqueous suspension of Raney nickel are mixed together. Over a period of 4 hours a slow moving stream of hydrogen gas is bubbled through the agitated mixture. The reaction system is then purged by bubbling nitrogen gas through it and filtered. The product retained on the filter is rinsed with methanol. The filtrate is evaporated to dryness, the residue obtained is dissolved in methylene chloride, dried over magnesium sulfate and evaporated to dryness to obtain 50 grams of 5,6-0-cyclohexylidene 3'-desoxy tetra-N-carbomethoxy neamine which may be used for the following step.

A sample chromatographed on silica with a mixture of chloroform-methanol (95:5) as eluant has the following characteristics:

Analysis: ($C_{26}H_{42}N_4O_{13}$); Calculated: C% 50.5, H% 6.85, N% 9.06, Found: C% 50.1, H% 6.9, N% 8.7; $[\alpha]_D^{20°}$ = +3° (C=0.85%, chloroform)

Thin layer chromatography (silica, chloroform-methanol 95:5): Rf 32 0.25

Stage D: 5,6-0-cyclohexylidene 4'-acetyl 3'-desoxy tetra-N-carbomethoxy neamine.

50 grams of the product obtained from the preceding stage was dissolved in 500 ml of pyridine containing 250 ml of acetic anhydride. The mixture is allowed to stand at room temperature and at the end of 5 hours, is evaporated to dryness while the liquid product is totally removed by means of toulene. 55 grams of 5,6-0-cyclohexylidene 4'acetyl 3'-desoxy tetra-N-carbomethoxy neamine which is used in the following step is obtained.

Thin layer chromatography (silica, chloroform-methanol 95:5): Rf =0.45

Stage E: 4'-acetyl 3'-desoxy tetra-N-carbomethoxy neamine:

55 grams of the product obtained in the preceeding stage is dissolved in 500 ml of acetic acid containing 20% water. The mixture is heated to 60° C and maintained at this temperature for 3 hours, then, after cooling, evaporated to dryness under vacuum. The residue obtained is chromatographed on silica using as the eluant a 96:4 mixture of chloroform and methanol. 23 grams of 4'-acetyl 3'-desoxy tetra-N-carbomethoxy neamine, $[\alpha]_D^{20°}$ = +60°5 (C = 0.55%, chloroform)

Thin layer chromatography (on silica with chloroform-methanol 95:5): Rf = 0.30

Stage F: 4-0-[2',6'-di-N-carbomethoxyamino 4'-0-acetyl 2',3',6'-tridesoxy D-ribohexopyranosyl] 6-0-[3''-(N-carbethoxy N-methyl) amino 2''-0-benzyl 3'',4'',6''-tridesoxy α, D-xylohexopyranosyl] 1,3-dimethyloxycarbonyl 2-desoxy streptamine:

3.1 grams of 1-0-acetyl 2-0-benzyl 3-[N-carbethoxy N-methyl] amino 3,4,6-tridesoxy D-xylohexopyranose was dissolved in 33 ml of dioxane containing 10% gaseous hydrochloric acid and 6.6 ml of acetyl chloride. The mixture is stirred for 2 hours at room temperature and the solvent evaporated under vacuum. The residue obtained is dissolved in 6.6 ml of dioxane and the thus obtained solution is poured into a solution at 60° C of 2.2 grams of 4'-acetyl 3'-desoxy tetra-N-carbomethoxy neamine in 77 ml of dioxane which also contained 3.3 grams of mercuric cyanide. The mixture was stirred for 4 and ½ hours at 60° C and then 3.3 more grams of mercuric cyanide were added to provide 3.1 grams of the chloro derivative of 1-0-acetyl 2-0-benzyl 3-[N-carbethoxy N-methyl] amino 3,4,6-tridesoxy D-xylohexopyranose. The mixture was stirred for an additional 17 hours at 60° C and then the dioxane was evaporated. An aqueous solution of sodium bicarbonate (45 grams per liter) was added followed by extraction with chloroform. After the organic phase was dried over magnesium sulfate and evaporated to dryness, the residue was chromatographed on silica and eluted with a mixture of chloroform and acetone (7:3). 2.8 grams of 4-0-[2',6'-di-N-carbomethoxyamino 4'-0-acetyl 2',3',6'-tridesoxy D-ribohexopyranosyl] 6-0-[3''-(N-carbethoxy N-methyl) amino 2''-0-benzyl 3'',4'',6''-tridesoxy α, D-xylohexopyranosyl] 1,3-dimethyloxy carbonyl 2-desoxy streptamine in the form of a white solid was obtained.

$[\alpha]_D^{20°} = +52°$ (C=0.55%, chloroform)

Thin layer chromatography (on silica with chloroform-acetone 7:3) Rf = 0.25.

Stage G: 4-0-[2',6'-diamino 2',3',6'-tridesoxy α, D-ribohexyopyranosyl]6-0-[3''-methylamino 3'',4'',6''-tridesoxy α, D-xylohexopyranosyl] 2-desoxy streptamine:

4.5 grams of the product of the preceding example was dissolved in 80 ml of ethanol containing a small amount of methylene chloride, 0.32 ml of concentrated hydrochloric acid and 2.7 grams of 10% palladium on carbon black.

The mixture was stirred in a hydrogen atmosphere for 1 and ½ hours. The catalyst was filtered off and the solution evaporated to dryness. The residue was chromatographically eluted on silica with a mixture of chloroform and methanol (95:5).

One gram of the pure product, obtained by thin layer chromatography with the preceding element (chloroform and methanol mixture) Rf 0.15, is dissolved in a mixture comprising 4 ml of ethanol, 8 ml of water and 7.87 grams barium hydroxide (hydrated baryta). The mixture is stirred for 4 hours at 90°–94° C, then cooled and the reaction mixture filtered. The filtrate is brought to a pH of 3 by means of normal sulfuric acid, separate the barium sulfate precipitated and neutralize the filtrate thus obtained by means of a basic ion exchange resin. The resin is separated and the filtrate dried. The residue obtained is purified by passing through a column of carboxylic type ion exchange resin in the ammonium form using as an eluant 0.15 N and then 0.5 N ammonium hydroxide.

The product eluted by the 0.5 N ammonium hydroxide is chromatographed on silica to separate the position 1 inch anomers using as eluant a mixture of chloroform-methanol-ammonium hydroxide (2-2-1). 58 mg of the β anomer and 143 mg of the α-anomer was obtained.

α-anomer $[\alpha]_D^{20°} = +124°$ (C=0.5% water)
Rf 0.5(silica, chloroform-methanol-ammonia 2-2-1)
β-anomer $[\alpha]_D^{20°} = 52°5$ (C=0.2% water)
Rf = 0.6 (silica, chloroform-methanol-ammonia 2-2-1)

1-0-acetyl 2-0-benzyl 3-(N-carbethoxy N-methyl) amino 3,4,6-tridesoxy D-xylohexopyranose used in Stage F may be obtained by the following example.

Stage 1. Ethyl 3-(N-carbethoxy N-methyl) amino 3,4,6-tridesoxy D-xylohexopyranoside:

67 grams of ethyl 3-(N-carbethoxy N-methyl) amino 3,4,6-tridesoxy 2-0-ethoxycarbonyl D-xylohexopyranoside (prepare according to J. Org. Chem., 1965, 30, 1287) are dissolved in 500 ml of ethanol, and then 200 ml of 2 N soda are added.

The mixture is stirred for an hour at room temperature, diluted with water and extracted with methylene chloride. The organic phase is washed with water and evaporated to dryness under vacuum. 57 grams of the product in the form of a yellow oil was obtained which is used in the following stage:

Stage 2: ethyl 2-0-benzyl 3-(N-carbethoxy N-methyl) amino 3,4,6-tridesoxy D-xylohexopyranoside:

12 grams of sodium hydride dispersed in mineral oil is suspended in 300 ml of tetrahydrofuran. A solution of 57 grams of the product of the preceding stage in 100 ml of tetrahydrofuran is added with stirring. The mixture is heated to boiling and refluxed for fifteen minutes, then cooled to 25° C. 29 ml of benzyl bromide is added and the mixture stands at room temperature for 15 hours. The mixture is diluted with water and extracted with ethyl acetate. After evaporation of the ethyl acetate an oil is obtained which is chromatographed on silica by means of a mixture of benzene and ethyl acetate '8-2). 60 grams of the desired product is obtained in the form of a white crystalline solid. M.P. 65° C.

Stage 3: 1-0-acetyl 2-0-benzyl 3-(N-carbethoxy N-methyl) amino 3,4,6-tridesoxy D-xylohexopyranose:

Gaseous hydrochloric acid is bubbled into a mixture of 600 ml acetic acid and 60 ml of acetic anhydride at 25° C until the mixture is saturated. 60 grams of the product obtained in the preceding stage was added and the mixture was allowed to stand for 16 hours at room temperature while maintaining bubbling of the gaseous hydrochloric acid. The mixture is then evaporated to dryness, under vacuum, without allowing the temperature of the product to go above 40° C.

The oil obtained is chromatographed on silica by means of a mixture of chloroform and acetone (9-1) as eluant.

60 grams of the product in the form of a white crystalline solid was obtained.

The pure α-anomer has been obtained by recrystallization from isopropyl ether and has a M.P. of 87° C.

Analysis: ($C_{19}H_{27}NO_6$); Calculated: C% 62.45 H% 7.45 N% 3.83. Found: C% 62.7 H% 7.7 N% 3.7.

EXAMPLE 2

4-0-[2',6'-diamino 2', 3', 6'-tridesoxy α, D-ribohexopyranosyl] 6-0-[3''-methylamino 3'',4'',6''-tridesoxy α, D-xylohexopyranosyl] 2-desoxy streptamine sulfate:

169 mg of the α-anomer obtained according to the preceding example was dissolved in 20 ml of water. The obtained solution was neutralized with decinormal sulfuric acid and the neutralization was followed by means of a pH meter. 16.5 ml of acid were used. The solution was filtered, the filtrate concentrated under vacuum and methanol added to precipitate the sulfate of the product.

230 mg of 4-0-[2',6'-diamino 2',3',6'-tridesoxy α, D-ribohexopyranosyl] 6-0-[3''-methylamino 3'',4'',6'' tridesoxy α, D-xylohexopyranosyl] 2-desoxy streptamine sulfate in the form of a white solid having the formula $C_{19}H_{39}N_5O_7$, 5/2 $H_2SO_4$ was obtained.

$[α]_D^{20°} = +89\%$ (C = 0.8% water) Rf = 0.5 (silica, chloroform-methanol-ammonia 2-2-1)

EXAMPLE 3

An injection preparation is prepared as follows:
Final product of Example 2 50 mg
Sterile aqueous excipient 1 ml
Pharmacalogical study of the compound of Example 2.
a. In vitro antibacterial activity The antibacterial activity has been measured in vitro by the dilution method in liquid medium.

A series of tubes is prepared in which is distributed the same quantity of nutritive medium. Increasing quantities of the antibiotic under study are distributed, then each tube is innoculated with a bacterial strain as indicated in the table. After a 18, 24 or 48 hour incubation in a 37° oven, inhibition of the bacterial growth is appraised by transillumination which determines the minimal inhibiting concentration (MIC) of the products expressed as μg/ml of base in the table. In the following table, the product of Example 2 is identified as Product A.

| STRAINS | Product A (MIC) | | |
|---|---|---|---|
| | 18 H | 24 H | 48 H |
| Staphylococcus aureus 40 481 | 0,1 | 0,1 | 0,2 |
| Staphylococcus aureus 40 511 | 0,2 | 0,6 | 1 |
| Staphylococcus aureus 40 821 | 0,1 | 0,1 | 0,1 |
| Staphylococcus aureus 38 691 | ≤0,05 | 0,1 | 0,1 |
| Streptococcus pyogenes A 561 | ≤0,05 | ≤0,05 | ≤0,05 |
| Streptococcus faecalis 99 F 74 | > 20 | — | — |
| Bacillus subtilis | ≤0,05 | ≤0,05 | ≤0,05 |
| Escherichia coli 9 911 | 0,6 | 0,6 | 0,2 |
| Escherichia coli 9 965 | 0,6 | 1 | 2 |
| Escherichia coli 156 | 0,4 | 0,6 | 1 |
| Salmonella anatum 23 348 | 1 | 3 | 15 |
| Salmonella typhimurium 420 | 2 | 5 | 20 |
| Salmonella typhimurium 1 374 | 1 | 5 | 10 |
| Enterobacter aerogenes Co86 | 0,6 | 0,6 | 0,6 |
| Enterobacter aerogenes Co11 | 0,4 | 0,4 | 1 |
| Serratia marcesens CoB 35 | 10 | 40 | 40 | b. In vivo antibacterial activity:

The antibacterial activity has been measured in vivo on an experimental Klebsiella Pneumonia infection.

40 male mice with a medium weight of 21 grams were divided in 4 series of 10 mice. An intraperitoneal infection with 0.5 ml of a Klebsiella Pneumonia No. 52145 culture in nutritive medium diluted to one thousandth with sterile water is conducted. Treatment is performed by a subcutaneous administration of the product of Example 2, (Product A) three times, (1 hour, 5 hours and 24 hours) after infection. The mortality rate at different times as indicated in the table was measured as well as the number of mice surviving after 8 days.

The results are summarized in the following table.

| Total Dose Administered (calculated on basis of free base) | 28 H | 31 H | Mortality at 45 H | 49 H | 70 H | 5 H | Survived to the eighth day |
|---|---|---|---|---|---|---|---|
| 0,03 mg | | | | | | 1 | 9 |
| 0,05 mg | | | | | | | 10 |
| 0,075 mg | | | | | | | 10 |
| Distilled Water | 1 | 1 | 6 | 1 | 1 | — | 0 |

The foregoing results clearly demonstrate the good activity of the product of Example 2 of the invention.

What is claimed is:

1. The 4-0-[2',6'-diamino 2', 3', 6'-tridesoxy α, D-ribohexopyranosyl] 6-0-[3''-methylamino 3'', 4'', 6''-tridesoxy α, D-xylohexopyranosyl] 2-desoxy streptamine having the formula:

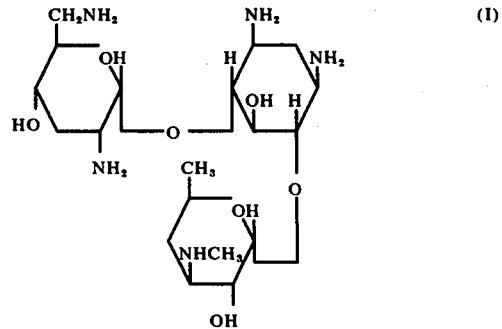

and its pharmaceutically acceptable salts.

2. The compound of claim 1 wherein the pharmaceutically acceptable salt is the hydrochloride, hydrobromide, nitrate, sulfate, phosphate, acetate, formate, benzoate, maleate, fumarate, succinate, tartrate, citrate, oxalate, benzylate, glyoxylate, aspartate, methanesulfonate or p-toluenesulfonate.

3. The compound of claim 2 which is 4-0-[2', 6'-diamino 2', 3', 6'-tridesoxy α, D-ribohexopyranosyl] 6-0-[3''-methylamino 3'', 4'', 6''-tridesoxy α, D-xylohexopyranosyl]2-desoxy streptamine sulfate.

4. A process for the preparation of the compound of claim 1 which comprises reacting a compound of the formula:

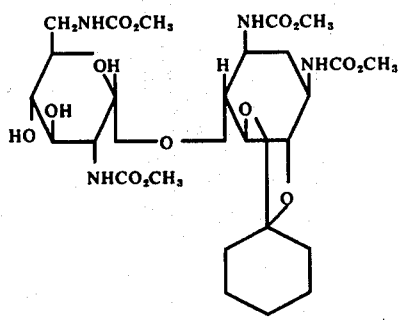

with tosyl chloride in the presence of an organic base to obtain a product of the formula:

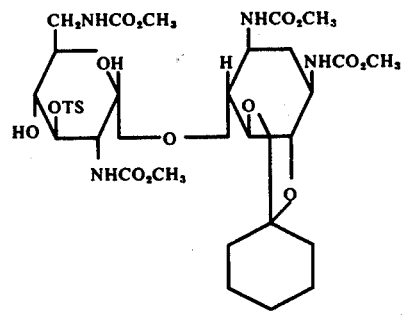

which is then treated with an alkaline iodide to obtain a product of the formula:

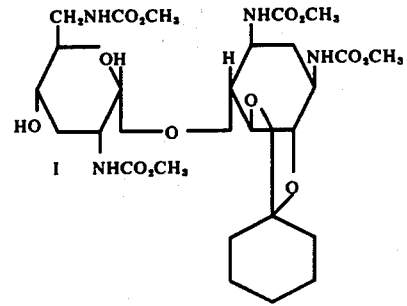

which is treated with hydrogen in the presence of a catalyst to obtain the product:

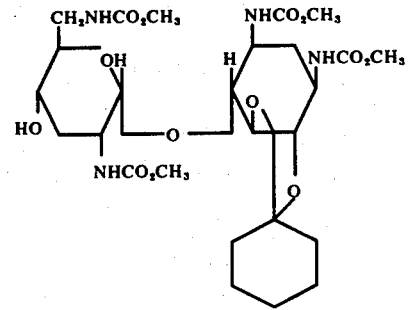

which was treated with acetic anhydride in the presence of an organic base to obtain the product having the formula:

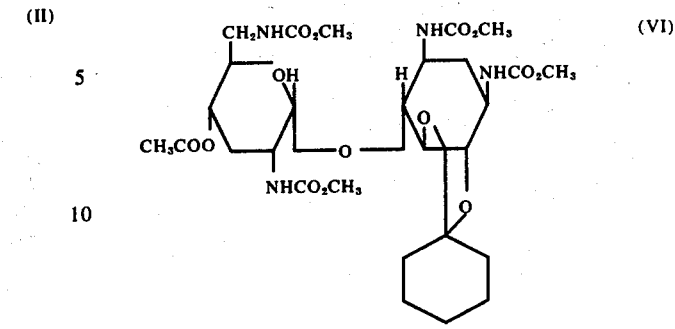

which was reacted with an acidic agent to obtain a product of the formula:

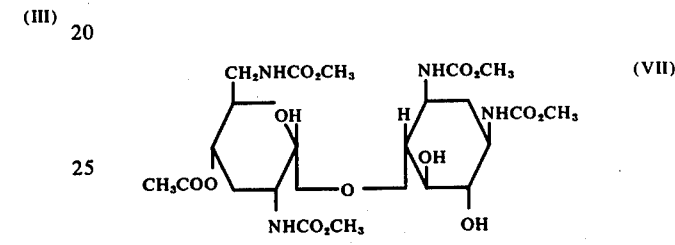

which was reacted with a product having the formula:

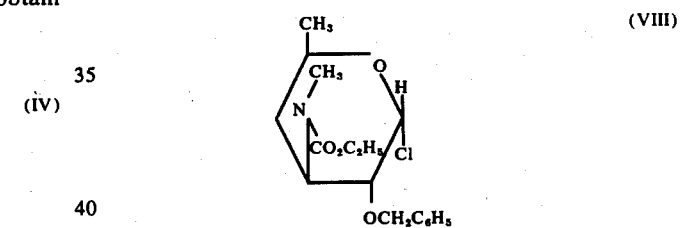

in the presence of a catalyst to obtain a condensation product as a mixture of α and β anomers having the formulae:

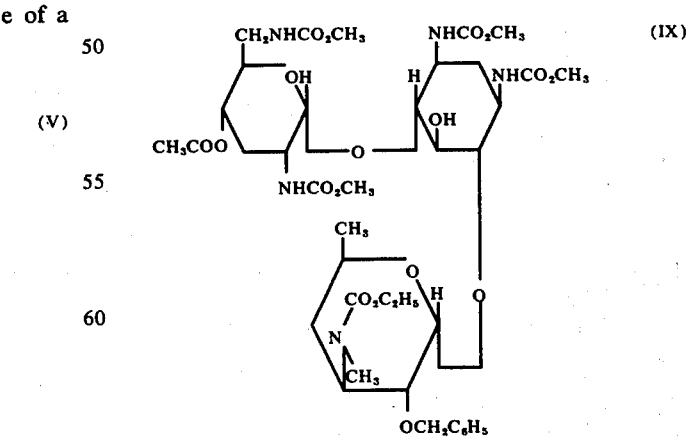

and

-continued

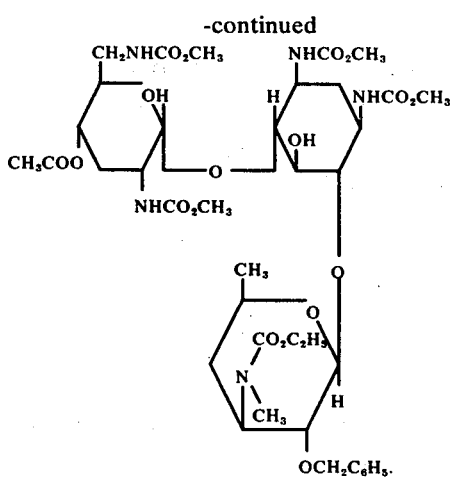

which mixture is treated with hydrogen in the presence of a catalyst and the blocked amine and hydroxyl functions liberated by treatment in an alkaline medium to obtain the mixture of products having the formulae:

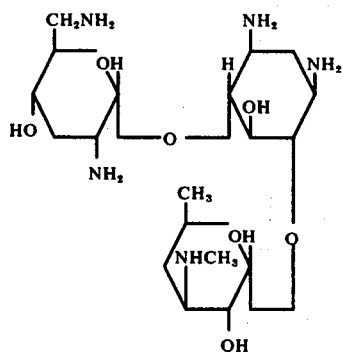

and

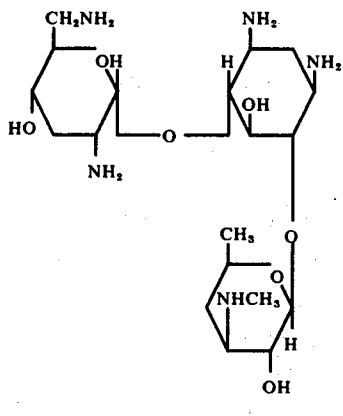

and the product of formula I is separated from the mixture, said compound may be converted to a pharmaceutically acceptable salt.

5. A pharmaceutical composition comprising a therapeutically effective amount of a compound of claim 1 and a carrier.

6. The composition of claim 5 wherein the compound is 4-0-[2', 6'-diamino 2', 3', 6'-tridesoxy α, D-ribohexopyranosyl] 6-0-[3''-methylamino 3'', 4'', 6''-tridesoxy α, D-xylohexopyranosyl] 2-desoxy streptamine sulfate.

7. The mixture of α and β anomers of formulae IX and IX':

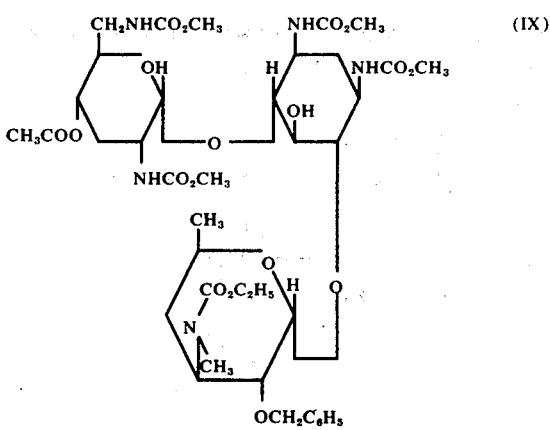

and

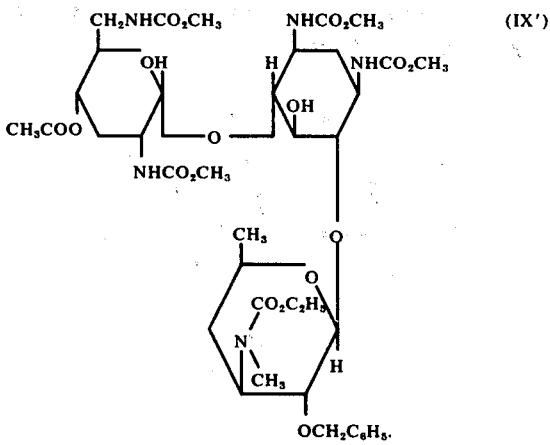

8. A method for treating bacteria infections in humans and animals comprising administering to humans and animals a therapeutically effective amount of the compound of formula I as claimed in claim 1 or one of its therapeutically compatible salts.

9. The method of claim 8 wherein the therapeutically compatible salt is the sulfate.

* * * * *

UNITED STATES PATENT OFFICE
CERTIFICATE OF CORRECTION

Patent No. 4,031,210　　　　　　　Dated June 21, 1977

Inventor(s)　　　JEAN-BERNARD CHAZAN et al

It is certified that error appears in the above-identified patent and that said Letters Patent are hereby corrected as shown below:

Column 3, lines 54 to 63, formula (VIII) should appear as follows:

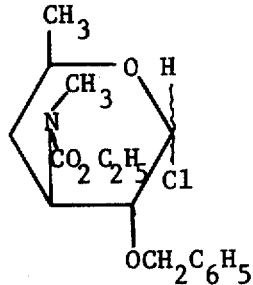

Column 6, lines 30 to 38, formula (XI) should appear as follows:

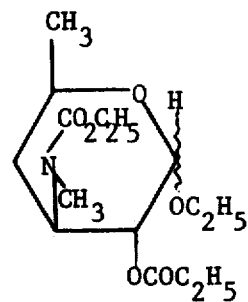

UNITED STATES PATENT OFFICE
CERTIFICATE OF CORRECTION

Patent No. 4,031,210          Dated  June 21, 1977

Inventor(s)          JEAN-BERNARD CHAZAN et al

It is certified that error appears in the above-identified patent and that said Letters Patent are hereby corrected as shown below:

Column 6, lines 42 to 50, formula (XII) should appear as follows:

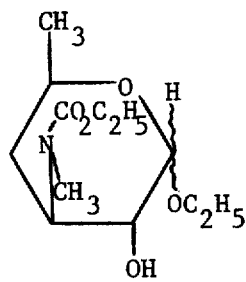

Column 6, lines 55 to 65, formula (XIII) should appear as follows:

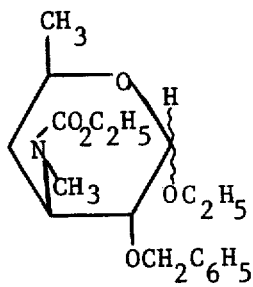

UNITED STATES PATENT OFFICE
CERTIFICATE OF CORRECTION

Patent No. 4,031,210      Dated June 21, 1977

Inventor(s) JEAN-BERNARD CHAZAN et al

It is certified that error appears in the above-identified patent and that said Letters Patent are hereby corrected as shown below:

Column 7, lines 1 to 10, formula (XIV) should appear as follows:

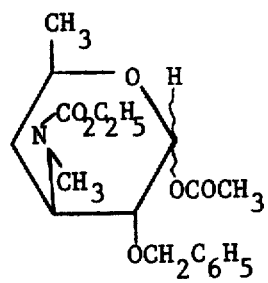

Signed and Sealed this

Twenty-eighth Day of November 1978

[SEAL]

Attest:

RUTH C. MASON  
Attesting Officer

DONALD W. BANNER  
Commissioner of Patents and Trademarks